United States Patent [19]

Mondet

[11] Patent Number: 6,001,338
[45] Date of Patent: Dec. 14, 1999

[54] COSMETIC USE OF NATURAL MICROFIBRILS AND A FILM-FORMING POLYMER AS A COMPOSITE COATING AGENT FOR HAIR, EYELASHES, EYEBROWS AND NAILS

[75] Inventor: Jean Mondet, Aulnay-sous-Bois, France

[73] Assignee: L'Oreal, France

[21] Appl. No.: 08/930,835

[22] PCT Filed: Jan. 28, 1997

[86] PCT No.: PCT/FR97/00165
§ 371 Date: Oct. 14, 1997
§ 102(e) Date: Oct. 14, 1997

[87] PCT Pub. No.: WO97/29734
PCT Pub. Date: Aug. 21, 1997

[30] Foreign Application Priority Data

Feb. 13, 1996 [FR] France ..................... 9607151

[51] Int. Cl.⁶ ............................................. A61K 7/04
[52] U.S. Cl. .................. 424/61; 424/70.1; 424/70.7; 424/70.11; 424/484; 424/486; 424/488
[58] Field of Search ................. 424/61, 70.1, 70.7, 424/70.11, 484, 486, 488

[56] References Cited

U.S. PATENT DOCUMENTS 4,891,213  1/1990  Gordon et al. .......................... 424/61

FOREIGN PATENT DOCUMENTS

| 0 379 409 | 7/1990 | European Pat. Off. . |
|---|---|---|
| 0 656 176 | 6/1995 | European Pat. Off. . |
| 2716887 | 9/1995 | France . |
| 63-275507 | 11/1988 | Japan . |
| 93-055602 | 8/1993 | Japan . |
| 07-196440 | 8/1995 | Japan . |
| 07-267827 | 10/1995 | Japan . |
| 93/10172 | 5/1993 | WIPO . |

OTHER PUBLICATIONS

A. Boldizar et al., "Prehydrolyzed Cellulose as Reinforcing Filler for Thermoplastics", Intern. J. Polymeric Mater., 11(4) :229–262 (1987).

Primary Examiner—Rebecca Cook
Attorney, Agent, or Firm—Finnegan, Henderson, Farabow, Garrett & Dunner, L.L.P.

[57] ABSTRACT

The present invention relates to the use of a polymer which forms a film in aqueous solution or in aqueous dispersion and of an aqueous suspension of microfibrils of natural origin in the form of elongate rigid particles, as a composite coating agent for the hair, the eyelashes, the eyebrows or the nails, in, and for the preparation of, a cosmetic or dermatological composition.

19 Claims, No Drawings

COSMETIC USE OF NATURAL MICROFIBRILS AND A FILM-FORMING POLYMER AS A COMPOSITE COATING AGENT FOR HAIR, EYELASHES, EYEBROWS AND NAILS

This is a 371 of PCT/FR97/00165 filed Jan. 28, 1997.

The present invention relates to the use of a polymer which forms a film in aqueous solution or in aqueous dispersion and of an aqueous suspension of microfibrils of natural origin in the form of elongate rigid particles, as a composite coating agent for the hair, the eyelashes, the eyebrows or the nails, in, and for the preparation of, a cosmetic or dermatological composition.

Cosmetic or dermatological compositions are mainly in a thickened liquid form. This type of presentation is very suitable for consumers: it usually corresponds to a practical preoccupation for the formulator: facilitating the uptake of the product from its packaging without any significant loss, limiting the diffusion of the product to the local area of treatment, being able to spread the product uniformly over the local area of treatment and being able to use it in amounts which are sufficient to obtain the desired cosmetic or dermatological effect.

This aim is of prime concern for formulations such as hair compositions, which need to be able to spread and distribute themselves uniformly along the keratin fibres, and not to run down the forehead, the nape of the neck, the face or into the eyes. This type of presentation is particularly sought for hair styling, maintenance and/or fixing products.

This aim is also important for aqueous compositions for making up the eyelashes or the eyebrows, which need to spread and distribute themselves uniformly along the eyebrows or eyelashes and not to run down the face, into the eyes or over the eyelids.

This aim is also important for aqueous nail varnishes which need to spread and distribute themselves uniformly over the nail without running onto the finger.

In particular, as regards hair styling and/or maintenance, transparent or translucent aqueous hair gels which can be taken up easily with the fingers without feeling sticky and which can spread easily onto the hair and form, after drying, a uniform and continuous sheath along the hair, without feeling sticky, are sought. The aqueous gels for hair styling and/or maintenance must also lead to a deposit having a sufficiently high adhesion to the hair during drying of the gel, at the risk of providing the hair with insufficient mechanical properties, too low a flexural strength, poor hold of the hair due to the sheath becoming partially or totally unstuck. The sheath obtained by drying the gel and the maintenance of the hairstyle resulting therefrom must also be resistant to ambient moisture (humid atmosphere, rain, swimming baths, etc.) and must be readily eliminated with shampoo in most of the applications.

Most of the standard hair gels, for example those based on film-forming acrylic polymers of the Carbopol or Pemulen type, have a tendency to form a heterogeneous and non-continuous deposit on the hair. They moreover feel sticky when taken up and on the hair. Furthermore, their water resistance and water moisture resistance is insufficient.

Other standard hair gels, in particular those based on guar gum, form a sheath around the strand of hair which tends to become unstuck in places during drying of the gel. Their resistance to water and to water moisture is insufficient.

The Applicant has discovered, unexpectedly, that the use of an aqueous suspension of specific microfibrils of natural origin in combination with a water-soluble film-forming polymer in solution or a water-insoluble film-forming polymer in dispersion makes it possible to obtain hair formulations in thickened form and in particular in the form of transparent or translucent aqueous gels which may be taken up easily with the fingers without feeling sticky, which can spread easily over the hair by virtue of a good rheofluidifying effect and which can form, after drying, a homogeneous and continuous sheath along the hair without feeling sticky. The sheath thus obtained by this combination is sufficiently adhesive on the hair during drying; furthermore, it is resistant to the mechanical attacking factors of the environment (friction, currents of air) as well as to ambient moisture. It is eliminated very easily on shampooing.

As regards aqueous products for making up the eyelashes and the eyebrows (mascaras or eye-liners), it is sought to prepare oil-in-water emulsions which are also in thickened form, or even in gel form. These formulations generally contain pigments in suspension and at least one film-forming polymer. Viscous products which can easily be spread onto the eyelashes or eyebrows without feeling sticky, both when applied and during drying of the formulation. Formulations which can form, after drying, a homogeneous and continuous sheath along the eyelashes or the eyebrows without feeling sticky are also sought. Within the context of aqueous mascaras, the sheath must allow an aesthetically satisfactory lengthening of the eyelashes. The said sheath should have good mechanical properties, in particular good resistance to rubbing to dryness, and should be sufficiently resistant to water, to ambient moisture and to facial cleansing agents.

The Applicant has discovered, unexpectedly, that the use of an aqueous suspension of specific microfibrils of natural origin in combination with a water-soluble film-forming polymer in solution or a water-insoluble film-forming polymer in dispersion makes it possible to obtain formulations for making up the eyelashes or the eyebrows which satisfy all these aims.

In the context of aqueous nail varnishes, it is sought to prepare pigment suspensions also in thickened form and in particular in the form of stable, very rheo-fluidifying aqueous gels which can be spread easily on the nail and which can rapidly form on the nail, after application and drying, a film of good rigidity without needing to use a coalescence agent and which do not feel sticky.

The Applicant has also discovered, unexpectedly, that the use of an aqueous suspension of specific microfibrils of natural origin in combination with a film-forming polymer in dispersion makes it possible to obtain make-up formulations for the nails which satisfy all these aims.

The subject of the present invention is thus the use of a film-forming polymer in aqueous solution or in aqueous dispersion and of an aqueous suspension of microfibrils of natural origin in the form of elongate rigid particles whose average length is greater than or equal to 80 nm and whose length/diameter ratio (shape factor) is preferably greater than or equal to 10, as composite coating agent for the hair, the eyelashes, the eyebrows or the nails, in, and for the preparation of, a cosmetic or dermatological composition.

Other objects of the invention will become apparent in the light of the description which follows.

The microfibrils of the invention are in the form of elongate rigid elementary particles with an average length preferably greater than or equal to 1 $\mu$m and a shape factor preferably greater than or equal to 30 and more particularly greater than or equal to 60.

Their degree of crystallinity is generally greater than or equal to 20% and preferably greater than 50%.

The microfibril suspensions used according to the invention come from many different sources.

The microfibrils of natural origin of the invention are preferably cellulose microfibrils of plant or animal origin or alternatively chitosan microfibrils extracted from chitin. They may also originate from bacterial transformations.

Among the cellulose microfibrils of plant origin, mention may be made of those extracted from parenchyma, those extracted from wood, those extracted from cereals such as wheat, those extracted from vegetables such as beetroot or those extracted from algae with cellulosic walls.

Among the cellulose microfibrils of animal origin, mention may be made, in particular, of those obtained from tunicin from the envelope of marine animals belonging to the tunicate family (for example the edible species Japanese *Halocynthia papillosa* or mediterranean *Microcosmus fulcatus*—violets).

A certain number of publications describe these microfibrils and their mode of preparation.

Mention may be made, in particular, of the article by V. Favier "Polymers for Advanced Technology" Vol. 6, 351–55 (1995) and French patent application No. 2 716 887 relating to cellulose microfibrils extracted from tunicin.

Mention may also be made of the article by Boldezar et al. "Prehydrolyzed Cellulose as reinforcing filler for thermoplasters" Intern. J. Polymeric Mater., 1987, Vol. 11, 229–262, relating to cellulose microfibrils extracted from wood.

Reference may also be made to the document by S. Salmon, AATCC, International Conference, 8–11, 10/95, p 296–306 (1995) for chitosan microfibrils.

Preferably, the aqueous suspensions of microfibrils of natural origin, in accordance with the invention, are stabilized by the presence of ionic charges which they carry at the surface. These surface charges preferably consist of sulphate ions, phosphate ions or carboxylate ions. They are obtained by an extraction process which is described in application WO 93/10172. This process consists in combining degradation of cellulose with passage through a high-speed homogenizer and a non-hydrolysing acid treatment, for example sulphuric acid or phosphoric acid, the purpose of which is to provide the microfibrils with surface ionic charges without, however, modifying the initial degree of polymerization of the cellulose. These surface charges may also be due to a pectin residue at the surface of the cellulose microfibrils.

The microfibril suspensions used according to the invention are generally translucent or even transparent at concentrations of less than or equal to 0.3% by weight. Above this value, they become opaque.

According to the cosmetic or dermatological application envisaged, the concentration of microfibrils of natural origin preferably ranges from 0.1 to 30% by weight and more preferably from 0.2 to 20% by weight relative to the total weight of the composition.

The water-soluble film-forming polymers used in accordance with the present invention may be chosen from those mentioned in patent applications EP-A-557,196 and EP-A-676,451. These polymers are more particularly used according to the invention in hair products, aqueous mascaras or aqueous care bases for the nails.

Mention may be made, for example, of: polyvinyl alcohol, hydroxyethylcellulose, the cellulose ethers generally used in cosmetics, guar gums, carob gums.

Depending on the desired type of application, the following will preferably be used
(i) either a synthetic film-forming water-soluble polymer of low glass transition temperature Tg, preferably less than or equal to 20° C.;

(ii) either a water-soluble film-forming polymer of natural origin (polysaccharides, cellulose derivatives) with a high Tg, generally greater than or equal to 40° C.

The microfibrils of natural origin are present in the microfibrils/water-soluble film-forming polymer mixture in proportions of less than or equal to 15% by weight and more preferably less than or equal to 10% by weight.

The aqueous dispersions of insoluble film-forming polymer used according to the invention are preferably chosen from hydrophobic polymer latices having a glass transition temperature Tg of less than or equal to 10° C. and more preferably less than or equal to 5° C.

The microfibrils of natural origin of the invention are present in the microfibrils/latex mixture in proportions of less than or equal to 15% by weight and more preferably less than or equal to 10% by weight.

These latices will be used more particularly in aqueous mascaras or nail varnishes.

The Applicant has discovered, surprisingly, that the microfibril suspension/film-forming polymer combination in a composition for making up the eyelashes containing pigments in suspension, substantially improves the lengthening of the eyelash when the microfibril concentration of the microfibrils/film-forming polymer mixture is greater than or equal to 6% by weight relative to the film-forming polymer.

The compositions of the invention contain a cosmetically or dermatologically acceptable medium, that is to say a medium which is compatible with the nails, the hair, the eyelashes or the eyebrows.

Depending on the cosmetic or dermatological application envisaged, the concentration of microfibrils of natural origin preferably ranges from 0.1 to 30% by weight and more preferably from 0.2 to 20% by weight relative to the total weight of the composition.

The cosmetically and/or dermatologically acceptable medium for the compositions according to the invention more particularly consists of water and optionally of cosmetically and/or dermatologically acceptable organic solvents (acceptable tolerance, toxicology and feel).

These solvents may be chosen from the group consisting of hydrophilic organic solvents, lipophilic organic solvents and amphiphilic organic solvents, or mixtures thereof.

Among the hydrophilic organic solvents, mention may be made, for example, of linear or branched lower monoalcohols having from 1 to 8 carbon atoms, such as ethanol, propanol, butanol, isopropanol and isobutanol; polyethylene glycols having from 6 to 80 ethylene oxides; polyols such as propylene glycol, butylene glycol, glycerol and sorbitol; monoalkyl or dialkyl isosorbide in which the alkyl groups have from 1 to 5 carbon atoms, such as dimethyl isosorbide; glycol ethers such as diethylene glycol monomethyl or monoethyl ether and propylene glycol ethers such as diproplylene glycol methyl ether.

As amphiphilic organic solvents, mention may be made of polyols such as isopropylene glycol; polypropylene glycol (PPG) derivatives, such as fatty acid esters of polypropylene glycol and fatty alcohol ethers of PPG, for instance PPG-23 oleyl ether and PPG-36 oleate.

As lipophilic organic solvents, mention may be made, for example, of fatty esters such as diisopropyl adipate, dioctyl adipate and alkyl benzoates.

In order for the cosmetic or dermatological compositions of the invention to be more pleasant to use (softer when applied, more nourishing and more emollient), it is possible to add a fatty phase to the medium of these compositions.

This fatty phase may contain one or more oils preferably chosen from the group consisting of:

volatile or non-volatile, linear, branched or cyclic, organo-modified or non-organomodified, water-soluble or water-insoluble silicones, mineral oils such as liquid paraffin and liquid petroleum jelly, oils of animal origin such as perhydrosqualene, oils of plant origin such as sweet almond oil, avocado oil, castor oil, olive oil, jojoba oil, sesame oil, groundnut oil, macadamia oil, grapeseed oil, rapeseed oil and coconut oil, synthetic oils such as purcellin oil and isoparaffins, fluoro and perfluoro oils.

The composition may also contain as fatty substance one or more fatty alcohols, fatty acids (stearic acid) or waxes (paraffin wax, polyethylene wax, carnauba wax, beeswax).

In a known manner, all the compositions of the invention may contain adjuvants that are common in the cosmetic and dermatological fields, other standard gelling agents and/or thickeners; polymers; emulsifiers; surfactants; moisturizers; emollients; sunscreens; hydrophilic or lipophilic active agents; anti-free-radical agents; bactericides; sequestering agents; antidandruff agents; antioxidants; preserving agents; fragrances; fillers; dyestuffs; plasticizers; coalescence agents. The amounts of these various adjuvants are those used conventionally in the fields considered.

Obviously, a person skilled in the art will take care to choose the optional compound(s) to be added to the compositions according to the invention such that the advantageous properties intrinsically associated with the compositions in accordance with the invention are not, or are substantially not, adversely affected by the addition envisaged.

The compositions according to the invention may be in any form which is suitable for the hair, the eyelashes, the eyebrows or the nails, in particular in the form of solutions of the lotion or serum type; in the form of aqueous gels; in the form of emulsions obtained by dispersion of a fatty phase in an aqueous phase (O/W) or, conversely, (W/O), of liquid or semi-liquid consistency such as milks or relatively smooth creams, and pastes. These compositions are prepared according to the usual methods.

The compositions according to the invention may be used as rinse-out or leave-in hair products, in particular to wash, care for or condition, to hold the style or to shape keratin fibres such as the hair.

They may be styling products such as hair-setting lotions, blow-drying lotions or fixing and styling compositions. The lotions may be packaged in various forms, in particular in vaporizers, pump-dispenser bottles or in aerosol cans in order to apply the composition in vaporized form or in the form of a mousse. Such packaging forms are indicated, for example, when it is desired to obtain a spray or mousse for fixing or treating the hair.

The compositions of the invention may also be shampoos and rinse-out or leave-in compositions, to be applied before or after shampooing, dyeing, bleaching, permanent-waving or straightening the hair.

The compositions in accordance with the invention may be make-up products, in particular:

aqueous products for coating the eyelashes and the eyebrows, such as "cream" mascaras or waterproof mascaras;

aqueous products for coating nails, such as nail care bases, varnish undercoats with standard solvent or aqueous nail varnishes.

The examples which follow serve to illustrate the invention without, however, being limiting in nature.

EXAMPLE 1

Preparation of an Aqueous Suspension of Cellulose Microfibrils Carrying Sulphate Surface Charges, Obtained from Tunicin After the pieces of envelope from violets have been coarsely cleaned, they are placed in 500 ml of aqueous 5% potassium hydroxide (KOH) solution overnight. They are then washed and blanched for 6 hours in a bath at 80° C., the bath being changed every two hours. This bath is composed of 300 ml of a chlorite solution (17 g of $NaClO_2$ in 1 l of distilled water) mixed with 300 ml of an acetate buffer solution (27 g of NaOH added to 75 ml of $CH_3COOH$ and made up to 1 l with distilled water). This blanching treatment is repeated 3 times; it makes the violet pieces completely white.

The pieces of cellulose are then disintegrated in a Waring Blender mixer for 20 minutes, the concentration of the pieces being about 5% in distilled water. An aqueous flocculating suspension of fragments of wall is thus obtained, which is diluted to about 1% and introduced in successive cycles into a Gaulin 15M8TA mechanical homogenizer. The pressure of the machine is raised to 600 bar in stages, in order to avoid blocking of the machine by the larger cellulose fragments. The temperature rise is monitored and care is taken to limit it to 70° C. After about 15 cycles, a homogeneous suspension containing small aggregates of fibres is obtained. A simple test of efficacy of the operation consists in observing the rise in the thickness of the product. As a guide, the desired result is reached when a consistency of petroleum jelly is obtained with suspensions having a titer of about 2% cellulose.

The suspension obtained from the homogenizer is then treated with sulphuric acid, in a proportion of 300 ml of concentrated (95%) sulphuric acid per 450 ml of suspension leaving the homogenizer. The whole mixture is maintained at 60° C. for 20 minutes. The suspension is then filtered through a sinter funnel (porosity 1) in order to remove the coarse aggregates, after which the cellulose fibrils are retained on a filter of porosity 4. This product is washed with distilled water and then with sodium hydroxide NaOH (0.1%) until the suspension is neutral, then again with distilled water. In this way, the cellulose is deposited on the filter in the form of an aqueous paste of viscous consistency. It is redispersed in water and the suspension is homogenized using a magnetic stirrer and then undergoes sonication (Branson Sonifier B12) for about 5 minutes. The final suspension is ready for use, fully homogeneous, non-flocculating and stable for several weeks.

EXAMPLE 2

Synthesis of a Water-Soluble Acrylic Copolymer with a Glass Transition Temperature of 3° C.

This is a copolymer obtained by radical polymerization of:

| | |
|---|---|
| Acrylic acid | 10% by weight |
| Isobutyl acrylate | 70% by weight |
| t-Butyl acrylate | 20% by weight |

The polymerization is carried out in solution in ethanol with initiation using azobisisobutyro-nitrile.

200 g of absolute ethanol, 100 g of the mixture of monomers and 2 g of azobisbutyronitrile are introduced into a 500 ml reactor with a central stirrer, a thermometer, a condenser and a tube for bubbling nitrogen through. Stirring is carried out at 250 revolutions/minute while bubbling nitrogen through. The mixture is heated gradually to reflux (78° C.) and is maintained at this temperature and under these conditions for 18 hours. After this time, the mixture is cooled to room temperature and the polymer is purified by precipitation in 5 l of petroleum ether. The precipitate is dried under vacuum at 45° C. to constant weight. 81 g of polymer are obtained, in a yield of 81%.

The acid number measured is 81.5.

The absolute viscosity as a 5% by weight solution of dimethylformamide at 34.6° C. is 1.7 cps.

The molecular weight at the top of the peak in the steric exclusion chromatograph is 36,800.

An aqueous solution of the composition below is prepared:

| | |
|---|---|
| Water-soluble film-forming polymer of Example 2 | 27.37 g |
| 2-Amino-2-methylpropanol (100% neutralization) | 3.53 g |
| Deionized water | 69.10 g |

EXAMPLE 3

Preparation of an Aqueous Mixture Consisting of the Combination of the Aqueous Suspension of Example 1 and the Polymer Solution of Example 2

The microfibril suspension of Example 1 is brought to a solids content of 2.34% by weight of microfibrils in order to make up 100 g of aqueous gel.

42.65 g of this gel (microfibril suspension) are taken and are mixed, with stirring, with 57.35 g of polymer solution of Example 1 in order to obtain an aqueous mixture capable of forming, after drying, a composite material containing 6% by weight of microfibrils.

An aqueous gel of the composition below is thus prepared:

| | |
|---|---|
| Water-soluble film-forming polymer of Example 2 | 15.7 % by weight |
| 2-Amino-2-methylpropanol (100% neutralization) | 2.0% by weight |
| Microfibrils of Example 1 | 1.0% by weight |
| Deionized water | 81.3% by weight |

EXAMPLE 4

Aqueous Mascara

A mascara is prepared by simple addition of the aqueous gel of Example 3 to a sufficient amount of pigments commonly used for mascaras. The mascara obtained is stable, homogeneous, allows eyelashes to be lengthened and is of good remanence to water. It can be removed easily with a cleansing product.

EXAMPLE 5

Hair-fixing Gel

A hair-fixing gel is prepared from the gel of Example 3. After evaporation, this product gives a film on the hair which has satisfactory fixing properties, is of good remanence to water and can be removed easily with shampoo.

EXAMPLE 6

Synthesis of a Hydrophilic Film-Forming Latex

This is a latex of composition:

| | |
|---|---|
| Acrylic acid | 10% by weight |
| Isobutyl acrylate | 70% by weight |
| t-Butyl acrylate | 20% by weight |

62.5 g of deionized water, 1.24 g of an aqueous 30.4% solution of alkyl ethoxysulphate surfactant sold under the name Abex JKB by the company Rhône Poulenc and 0.19 g of potassium persulphate are introduced into a reactor fitted with a central mechanical stirrer, a thermometer and a condenser. The mixture is brought to a temperature of 80° C. with rapid stirring.

In parallel, the two so-called "cast" solutions $S_1$ and $S_2$ below are prepared:

| | |
|---|---|
| Cast $S_1$ (monomer solution): | |
| Acrylic acid | 12.5 g |
| Isobutyl acrylate | 87.5 g |
| t-Butyl acrylate | 25 g |
| Dodecanethiol | 1.25 g |
| Cast $S_2$: | |
| Deionized water | 312.5 g |
| Aqueous 30.24% Abex JKB solution | 11.16 g |
| Potassium persulphate | 0.55 g |

When the aqueous solution in the reactor has reached 80° C., 10% of the solution $S_1$ is added and the mixture is left to react for 15 minutes. The remainder of the solution $S_1$ and the solution $S_2$ are then run in simultaneously over a period of 4 hours and at a constant flow rate. At the end of the two simultaneous additions, the temperature of the reaction medium is increased to 85° C. and is maintained at this temperature for 30 minutes.

The mixture is allowed to cool to room temperature with stirring. It is filtered through Nylon gauze.

A dispersion of polymer particles having the following characteristics is obtained:
Average particle size: 230 nm
Particle size polydispersity measured by quasi-elastic light scattering with a machine of the Coulter N4 SD type: <0.1
Solids content in ventilated oven at 80° C. to constant weight: 25%
Molecular weight at the top of the peak in the steric exclusion chromatograph: 70,000
Glass transition temperature measured by DSC: −7° C.

The aqueous polymer dispersion obtained is concentrated on a rotary evaporator to a final solids content of 50.36%.

EXAMPLE 7

Preparation of an Aqueous Mixture Consisting of the Combination of the Aqueous Suspension of Example 1 and the Polymer Dispersion of Example 6

The microfibril suspension of Example 1 is brought to a solids content of 2.34% by weight of microfibrils in order to make up 100 g of aqueous gel.

56.32 g of this gel (microfibril suspension) are taken and are mixed, with stirring, with 43.68 g of polymer dispersion of Example 6 in order to obtain an aqueous mixture which can form, after drying, a composite material containing 5.7% by weight of microfibrils relative to the polymer.

An aqueous gel of the composition below is thus prepared:

| | |
|---|---|
| Film-forming polymer of Example 6 | 22 g (solids content) |
| 2-Amino-2-methylpropanol (100% neutralization) | qs pH 7 |
| Microfibrils of Example 1 | 1.32 g |
| Deionized water | 76.68 g |

EXAMPLE 8

Aqueous Mascara

A mascara is prepared by simple addition of the aqueous gel of Example 7 to a sufficient amount of pigments commonly used for mascaras. The mascara obtained is stable, homogeneous, allows the eyelashes to be lengthened and is of better remanence to water than the mascara of Example 4. It is easily removed with cleansing product.

EXAMPLE 9

Synthesis of a Hydrophobic Film-Forming Latex

This is a latex of composition:

| | |
|---|---|
| Isobutyl acrylate | 63.8% by weight |
| t-Butyl acrylate | 36.2% by weight |

The process is performed under the same conditions as those of Example 6.

A dispersion of polymer particles is obtained having the following characteristics:

Average particle size: 250 nm
Particle size polydispersity measured by quasi-elastic light scattering with a machine of the Coulter N4 SD type: <0.1
Solids content in a ventilated oven at 80° C. to constant weight: 24.8%
Molecular weight at the top of the peak in the steric exclusion chromatograph: 65,000
Glass transition temperature measured by DSC: −3° C.

The aqueous polymer dispersion obtained is concentrated on a rotary evaporator to a final solids content of 49.86%.

EXAMPLE 10

Preparation of an Aqueous Mixture Consisting of the Combination of the Aqueous Suspension of Example 1 and the Polymer Dispersion of Example 9

The microfibril suspension of Example 1 is brought to a solids content of 3.5% by weight of microfibrils in order to make up 100 g of aqueous gel.

42.86 g of this gel (microfibril suspension) are taken and are mixed, using a shear mixer of the Raineri type, with 57.14 g of polymer dispersion of Example 9 in order to obtain an aqueous gel of the composition below:

| | |
|---|---|
| Film-forming polymer of Example 9 | 28.5 g (solids content) |
| Microfibrils of Example 1 | 1.5 g |
| Deionized water | 70.0 g |

The dispersion obtained contains 5% by weight of microfibrils relative to the weight of the polymer.

EXAMPLE 11

Aqueous Nail Varnish

A varnish is prepared by dispersing, with shear mixing, 1 g of pigments commonly used for varnishes, in the aqueous gel of Example 10.

The varnish obtained is stable, easy to spread on account of a very rheo-fluidifying nature, and gives, after drying, a shiny film of good flexibility with no soft nature nor any surface stickiness. The deposit obtained on the nail is scratchproof, chip-proof, adheres well to the nail and has good resistance to attack by water and aqueous solutions of detergents or of surfactants.

I claim:

1. A process for the preparation of a cosmetic or dermatological composition comprising combining at least one film-forming polymer in aqueous solution or in aqueous dispersion, with an aqueous suspension of microfibrils of natural origin, said microfibrils having an average length greater than or equal to 80 nm and a shape factor greater than or equal to 10:1, wherein said polymer and said microfibrils are present together in an amount effective to act as a coating agent for the hair, the eyelashes, the eyebrows or the nails.

2. The process according to claim 1 wherein said coating agent forms a composite deposit after drying.

3. The process according to claim 1 wherein said microfibrils have an average length greater than or equal to 1 μm and a shape factor greater than or equal to 30:1.

4. The process according to claim 3 wherein said shape factor is greater than or equal to 60:1.

5. The process according to claim 1 wherein said microfibrils have a degree of crystallinity greater than or equal to 20%.

6. The process according to claim 5 wherein said degree of crystallinity is greater than or equal to 50%.

7. The process according to claim 1 wherein said microfibrils are cellulose microfibrils of plant or animal origin, chitosan microfibrils or microfibrils originating from bacterial transformations.

8. The process according to claim 7 wherein said cellulose microfibrils are selected from microfibrils extracted from parenchyma, from wood, from cereals, from vegetables, from algae with cellulosic walls and from tunicin.

9. The process according to claim 1 wherein said microfibrils carry surface ionic charges.

10. The process according to claim 9 wherein said surface ionic charges are sulphate ions, carboxylate ions or phosphate ions.

11. The process according to claim 1 wherein the microfibril concentration is less than or equal to 15% by weight relative to the amount of film-forming polymer.

12. The process according to claim 11 wherein said microfibril concentration is less than or equal to 10% by weight relative to the amount of film-forming polymer.

13. The process according to claim 1 wherein said at least one film-forming polymer is selected from synthetic film-forming polymers with a Tg of less than or equal to 20° C. and film-forming polymers of natural origin with a Tg of greater than or equal to 40° C.

14. The process according to claim 1 wherein said at least one film-forming polymer is in aqueous dispersion and is selected from hydrophobic polymer latices with a Tg of less than 10° C.

15. The process according to claim 14 wherein said Tg is less than 5° C.

16. The process according to claim 1 wherein said cosmetic or dermatological composition is a hair product to wash, care for, condition, maintain or hold the shape of the hair.

17. The process according to claim 1 wherein said cosmetic or dermatological composition is a make-up product for the eyelashes or the eyebrows.

18. The process according to claim 17 wherein the microfibril concentration is greater than or equal to 6% by weight relative to the amount of film-forming polymer.

19. The process according to claim 1 wherein said cosmetic or dermatological composition is a product to make up or care for the nails.

* * * * *